(12) United States Patent
Cho

(10) Patent No.: US 11,058,840 B2
(45) Date of Patent: Jul. 13, 2021

(54) RETRACTABLE RESPIRATORY MASK

(71) Applicant: MAKRITE INDUSTRIES INC., New Taipei (TW)

(72) Inventor: Shih-shiung Cho, Taipei (TW)

(73) Assignee: MAKRITE INDUSTRIES INC., New Taipei (TW)

( * ) Notice: Subject to any disclaimer, the term of this patent is extended or adjusted under 35 U.S.C. 154(b) by 344 days.

(21) Appl. No.: 16/251,027

(22) Filed: Jan. 17, 2019

(65) Prior Publication Data

US 2020/0230342 A1    Jul. 23, 2020

(51) Int. Cl.
*A61M 16/06*    (2006.01)
*A62B 23/02*    (2006.01)

(52) U.S. Cl.
CPC ..... *A61M 16/0683* (2013.01); *A61M 16/0605* (2014.02); *A61M 2202/0208* (2013.01); *A61M 2210/0618* (2013.01); *A62B 23/025* (2013.01)

(58) Field of Classification Search
CPC .............. A61M 16/06; A61M 16/0605; A61M 16/0611; A61M 16/0616; A61M 16/0622; A61M 16/0683; A62B 18/02; A62B 18/025; A62B 18/04; A62B 18/06; A62B 23/02; A62B 23/025; A62B 9/06
See application file for complete search history.

(56) References Cited

U.S. PATENT DOCUMENTS

| | | | | | |
|---|---|---|---|---|---|
| 4,562,837 | A | * | 1/1986 | Schlobohm | A62B 23/02 128/206.17 |
| 5,121,745 | A | * | 6/1992 | Israel | A61M 16/06 128/202.28 |
| 5,148,803 | A | * | 9/1992 | Schlobohm | A62B 18/025 128/205.27 |
| 5,515,846 | A | * | 5/1996 | Drews | A62B 18/02 128/201.25 |
| 2007/0144513 | A1 | * | 6/2007 | Park | A62B 18/084 128/202.26 |
| 2016/0184544 | A1 | * | 6/2016 | Patel | A61M 16/0683 128/206.24 |
| 2016/0303405 | A1 | * | 10/2016 | Elliott | A61B 5/14542 |
| 2019/0175863 | A1 | * | 6/2019 | Hocking | A61M 16/0616 |

\* cited by examiner

*Primary Examiner* — Joseph D. Boecker

(57) ABSTRACT

A retractable respiratory mask of the present invention comprise a worn portion, a filter portion adapted to connect with a filter member, and a retractable portion; the retractable portion connected between the worn portion and the filter portion comprises a first bend portion, a second bend portion and a displacement section. The two bend portions are spaced apart from each other and the displacement section is connected between the two bend portions. The retractable respiratory mask of the present invention can change the relative position between the two bend portions by folding over the displacement section. The retractable respiratory mask shows an extended shape when the first bend portion and the second bend portion are orderly arranged in an extending direction, and conversely shows a contracted shape when two bend portions are arranged along the opposite direction. By doing so, the mask can be folded up to reduce entire volume.

5 Claims, 6 Drawing Sheets

RETRACTABLE RESPIRATORY MASK

FIELD OF THE DISCLOSURE

The present disclosure relates to a respiratory mask, and more particularly, to a respiratory mask capable of folding and expanding to reduce storage volume.

BACKGROUND

Oxygen in the air is an indispensable substance for human beings to survive. However, in addition to the oxygen that is necessary for human survival, there are many substances that harmful to the human's body mixing in the air. Therefore, an air filtering means, such as a mouth mask or a face mask, which is conveniently carried and can be placed onto the nose and mouth to block dirt in the air, is required.

Wherein, the existing mouth mask/face mask is mainly developed in two directions, one of the two directions is to combine filter materials that responds to different pollutants in the environment to make a filtration/adsorption layer of a mask, in order to filter out as much dirt as possible in the air. However, this will greatly increase the thickness of a mouth mask/face mask, so this kind of mouth mask/face mask is generally made by first combining various filtration/adsorption layers to form a canister, and then making the entire body of the mask with an airtight material, and arranging an opening onto which the canister is mounted on the mouth mask/face mask. Through restricting the air entry, the air must pass through the canister when entering the mouth mask/face mask, the volume (thickness) of the mouth mask/face mask body reduces. Furthermore when wearing, since the weight of the canister needs to be supported by the mouth mask/face mask itself, the mouth mask/face mask must have a certain thickness in order to maintain sufficient support. And such a mouth mask/face mask does not deform easily, therefore, will be directly formed as three-dimensional one for fitting to the face, and thus such a mouth mask/face mask will be difficult to carry because of its thickness and shape.

In the other direction, as a usual disposable mask, in order to be folded like a paper and be carried easily, the thickness of the mask reduces by reducing the number of filtration/adsorption layers, so the mask can be folded and deformed to fit to the shape of the face. However, doing so would surely make the filtration/adsorption effect less than the mouth mask/face mask using canister as described above.

SUMMARY

The main purpose of the present invention is to provide a retractable respiratory mask, able to be folded up for reducing the overall volume, and be conveniently arranged to transport, used and stored.

To achieve above purpose, the retractable respiratory mask of the present invention comprise a worn portion, a filter portion and a retractable portion; the worn portion, by a surrounding wall, forms an opening toward an extending direction, and the surrounding wall is arranged with a fitting wall adapted to contact a face of a user; the filter portion is adapted to connect with a filter member; the retractable portion connected between the surrounding wall and the filter portion is able to make a deformation between an extended shape and a contracted shape, such that the filter portion can optionally move away from or close to the worn portion; the retractable portion comprises a first bend section, a second bend section and a displacement section, wherein the first bend section and the second bend section are spaced apart from each other, and the displacement section is connected between the first bend section and the second bend section.

As for the way the retractable respiratory mask is folded, wherein the retractable respiratory mask can change the relative position between first bend section and the second bend section by folding over the displacement section. The extended shape is where the first bend section and the second bend section are orderly arranged in the extending direction, while the contracted shape is where the first bend section and the second bend section are arranged along the direction opposite to the extending direction.

As for the form of the retractable respiratory in one preferable embodiment, the circumference of the first bend section is longer than the circumference of the second bend section, such that the retractable respiratory mask of the extended shape shows a form of being tapered from the worn portion along the extending direction.

The surrounding wall of the worn portion surrounds an accommodation space. When retractable respiratory mask is in the extended shape, the displacement section is away from the accommodation space. When the retractable respiratory mask is in the contracted shape, the displacement section enters the accommodation space.

As for the detail configuration of retraction, in the preferable embodiment, the retractable portion is composed of the same material, and the thickness of the first bend section and the second bend section is smaller than the thickness of the displacement section. When the retractable respiratory mask encounters external force, difference in thickness generates a stress concentration phenomenon, and thus bending first happens at the first bend section and the second bend section.

Furthermore in remaining detail configuration, in one preferable embodiment, the filter portion has a plane and a wall surface at the periphery of the plane. The plane is arranged with a first one-way valve for departure of air and a second one-way valve for entry of air.

While in another preferable embodiment, the filter portion has a plane and a wall surface at the periphery of the plane. The plane is arranged with a first one-way valve for departure of air, while the wall surface is arranged with at least one second one-way valve for entry of air.

As can be seen from above description, the present invention features two bend sections arranged with the retractable respiratory mask for easily deforming, such that bending first happens at the two bend sections when the mask encounters the force, and a displacement portion as a part of the mask between the two bend sections can fold over into an accommodation space surrounded by worn portion as another part of the mask. This makes a deformation from an extended shape to a contracted shape. Therefore, even the retractable respiratory mask requires a certain thickness and a three-dimensional shape to support the weight of the filter having a stronger filtering effect, but the storage volume of the retractable respiratory mask also can be reduced by folding up.

DETAILED DESCRIPTION OF PREFERRED EMBODIMENTS

Figure 1:
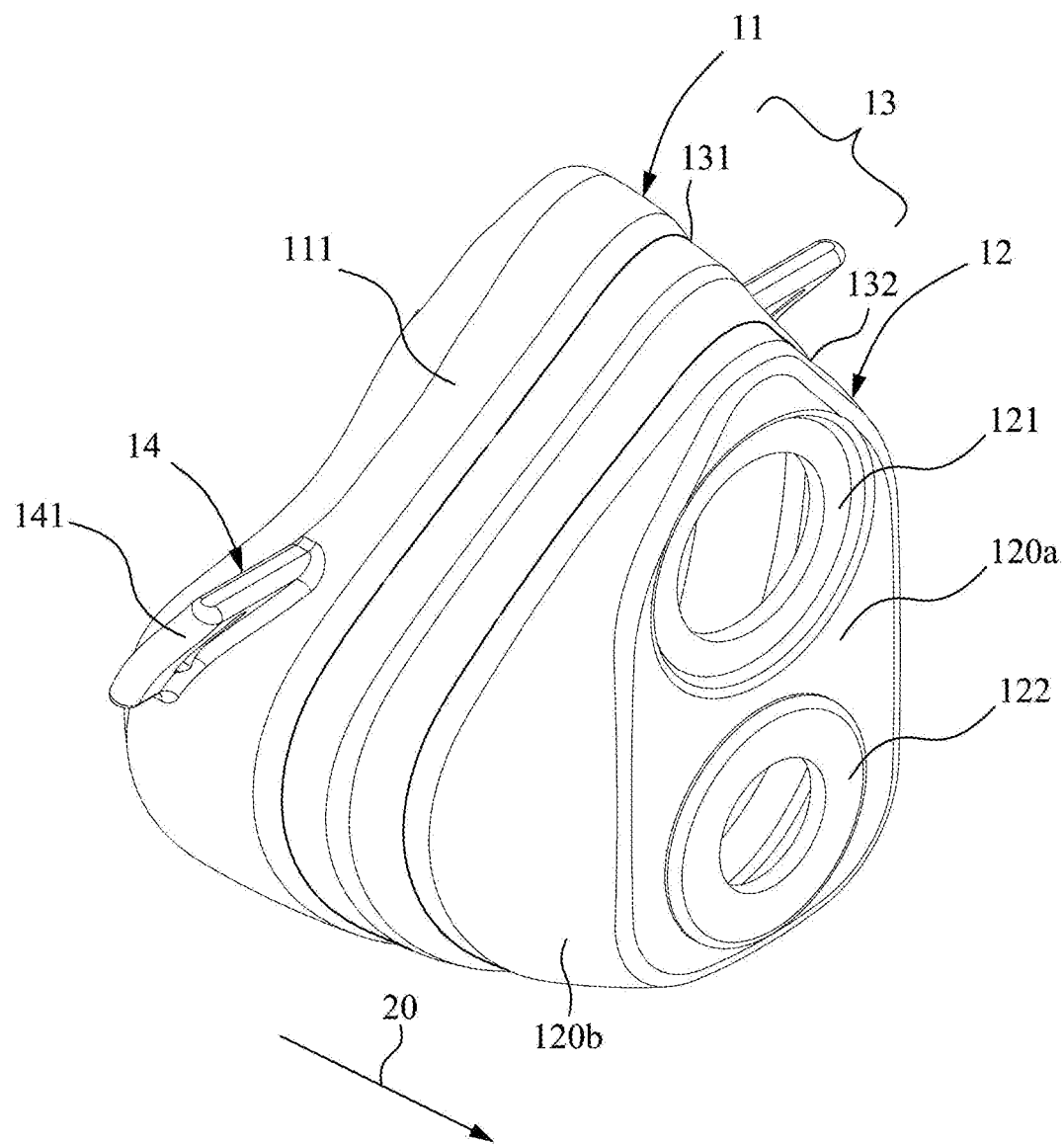
FIG. 1 is a schematic illustrating three dimensional view of the retractable respiratory mask in an extended shape of the present invention according to first preferable embodiment.

In order to further understand the structure, usage and features of the present disclosure more clearly, the present disclosure is described in detail below with references to the accompanying drawings and specific preferred embodiments.

Please refer to FIGS. 1 to 4. In first preferable embodiment, the retractable respiratory mask 10 of the present invention comprises a worn portion 11, a filter portion 12 and a retractable portion 13.

The worn portion 11 forms a surrounding wall 111 which has a size able to cover a mouth and a nose of a user. An accommodation space 112 is formed within the surrounding wall 111 and the surrounding wall 111 has an opening 113 communicating with the accommodation space 112, such that the face of the user can enter the accommodation space 112 via the opening 113. One end of the surrounding wall 111 near the opening 113 is arranged with a fitting wall 114, and the other one is adapted to connect with the retractable portion 13.

Figure 2:
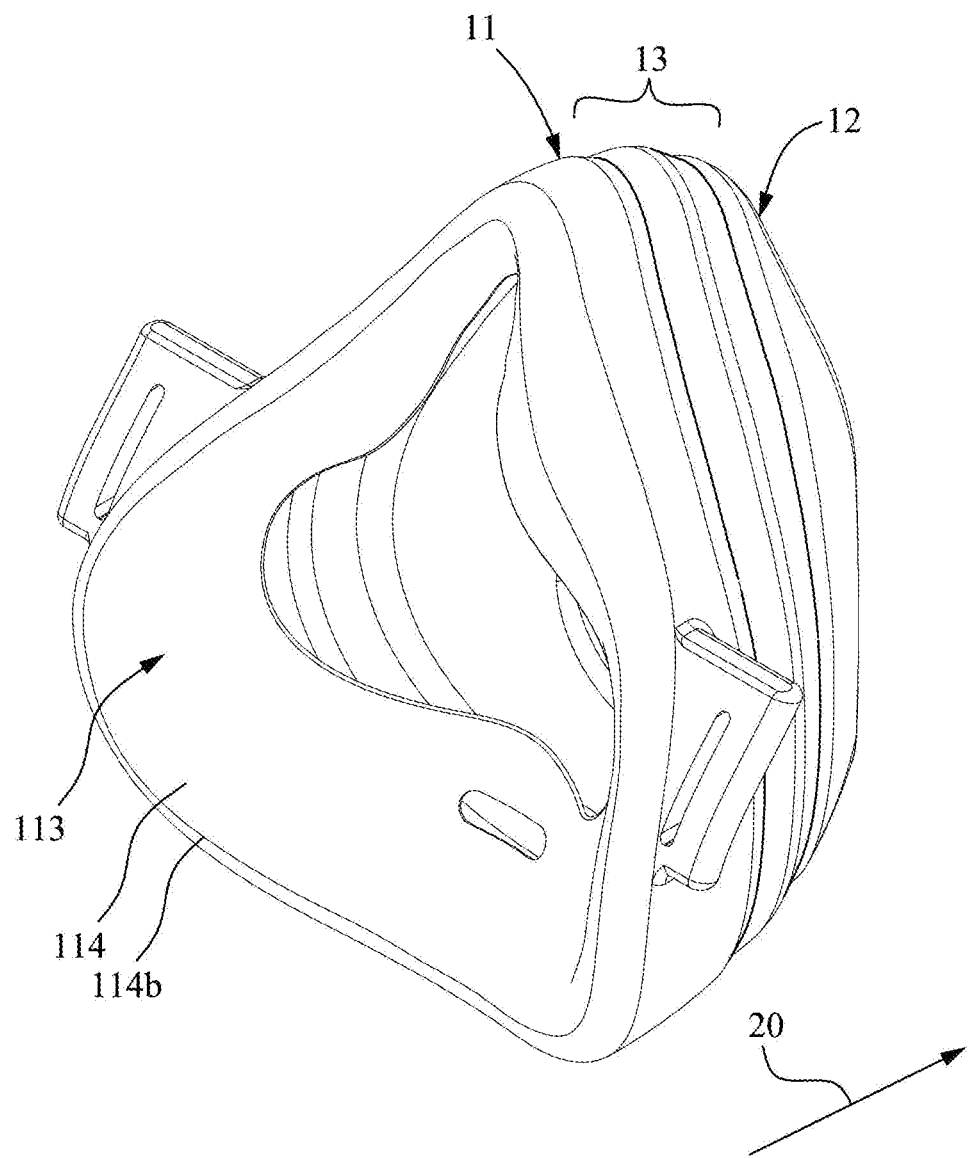
FIG. 2 is a schematic illustrating rear three dimensional view of the embodiment in FIG. 1.
Figure 3:
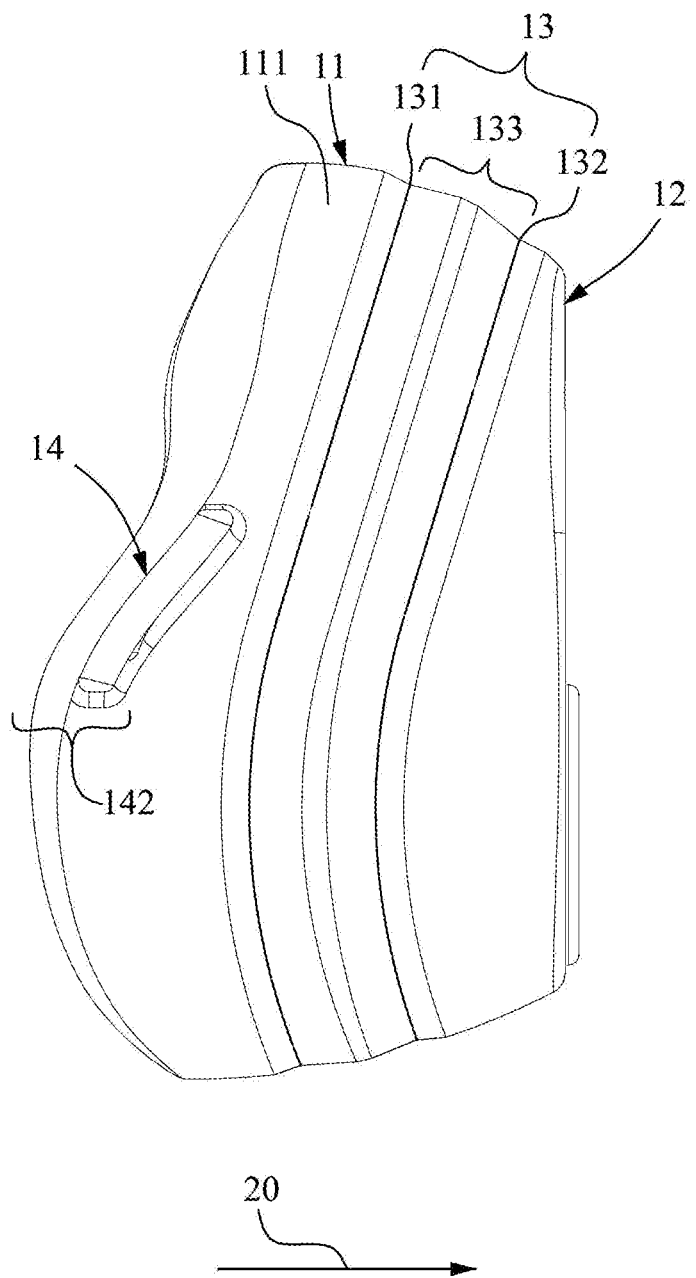
FIG. 3 is a schematic illustrating side view of the embodiment in FIG. 1.
Figure 4:
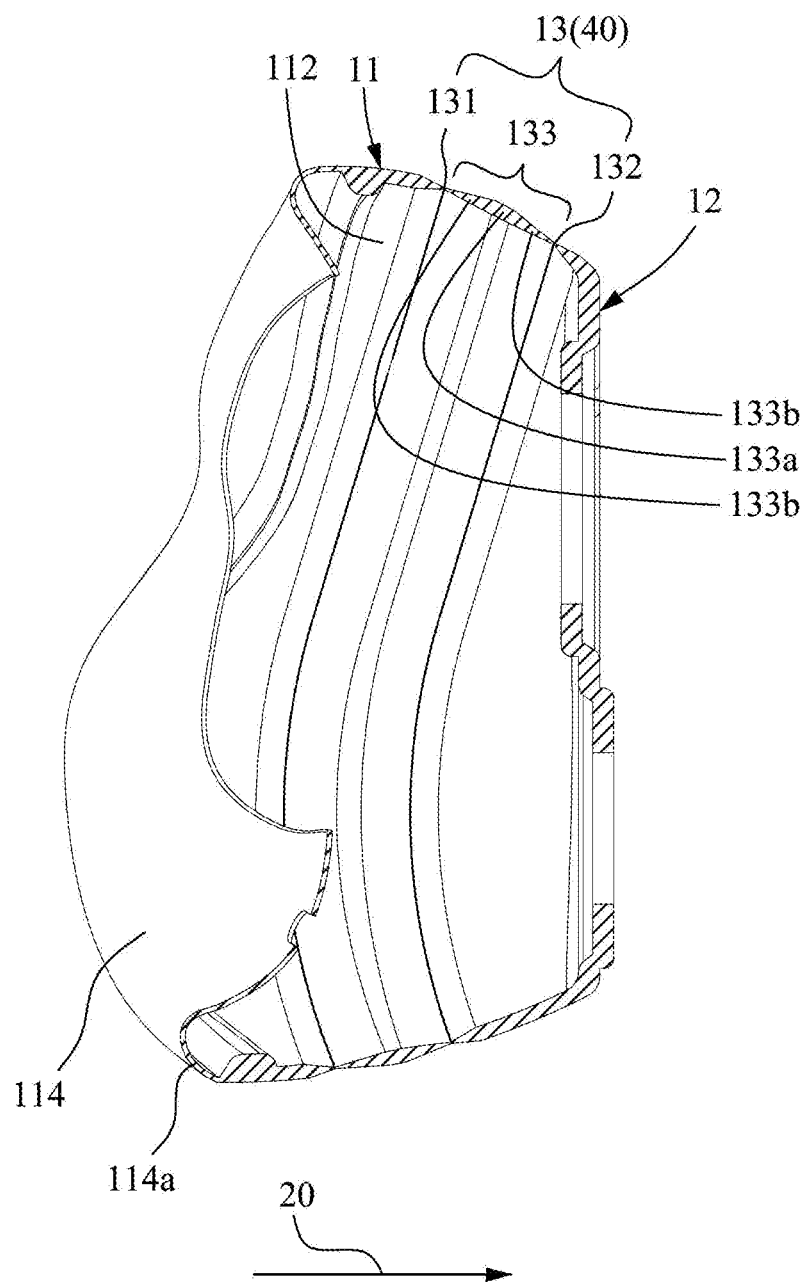
FIG. 4 is a schematic illustrating sectional view of the embodiment in FIG. 1.

As shown in FIGS. 2 to 4. In the present embodiment, a fold-up wall 114a is arranged between the fitting wall 114 and the surrounding wall 111. Wherein the fitting wall 114 extends toward the center of the opening 113 from the surrounding wall 111, such that a funnel structure is formed at the opening 113, and the surface of the fitting wall 114 forms a fitting surface 114b which contacts the face of the user. Therefore the airtightness of the retractable respiratory mask 10 can be maintained by the fitting wall 114 and the fold-up wall 114a pushing the face of the user, even if the contour of the face does not completely conform to that of the surrounding wall 111 when the user wears the retractable respiratory mask 10.

The filter portion 12 has a plane 120a and a wall surface 120b at the periphery of the plane 120a. In the present embodiment, the plane 120a is arranged with a first connecting portion 121 and a second connecting portion 122. The first connecting portion 121 is configured to be equipped with a first one-way valve 120d allowing air to leave the respiratory mask 10 in one single direction (please refer to FIG. 6), for quickly discharging air away the retractable respiratory mask 10 and preventing air from entering the retractable respiratory mask 10 from the first connecting portion 121; the second connecting portion 122 is adapted to connect with a filter member 120c (for conveniently showing the configuration of the mask 10, the filter member 120c is not shown in FIGS. 2 to 5, and only one of them is shown in the schematic illustrating of FIG. 6).

Wherein, there is no limitation on the first connecting portion 121 and the second connecting portion 122 in the present invention, and besides no limitation on the form of the filter member 120c. Therefore, during implementation, the second connecting portion 122 first may be arranged with a second one-way valve 120e for entry of air, and the filter member 120c may be connected to the second connecting portion 122 by being mounted on the second one-way valve 120e (for conveniently showing, please refer to FIG. 6 with a similar structure.); the filter member 120c and the first one-way valve 120d may use existing products, while the second connecting portion 122 and the second one-way valve 120e may be designed as use requirements.

In the present embodiment, the retractable portion 13 connected between the surrounding wall 111 and the filter portion 12 is composed of the same flexible material. The retractable portion 13 comprises a first bend section 131, a second bend section 132 and a displacement section 133. The first bend section 131 and the second bend section 132 are spaced apart from each other. And the displacement section 133 is connected between the first bend section 131 and the second bend section 132.

Figure 5:
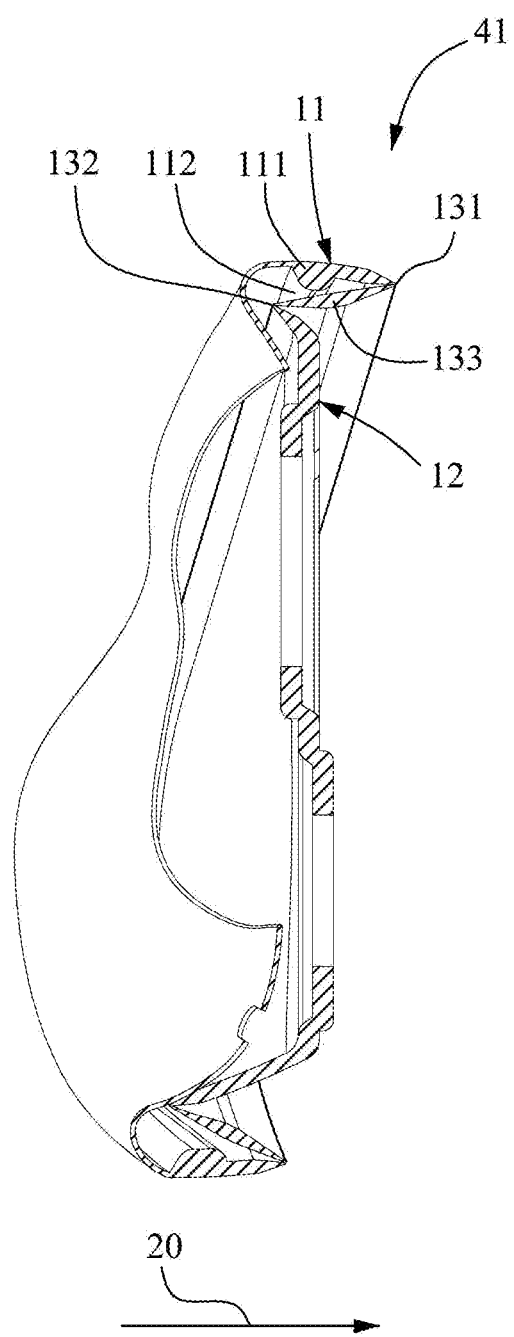
FIG. 5 is a schematic illustrating the retractable respiratory mask in an contracted shape of the present invention according to first embodiment.
Figure 6:
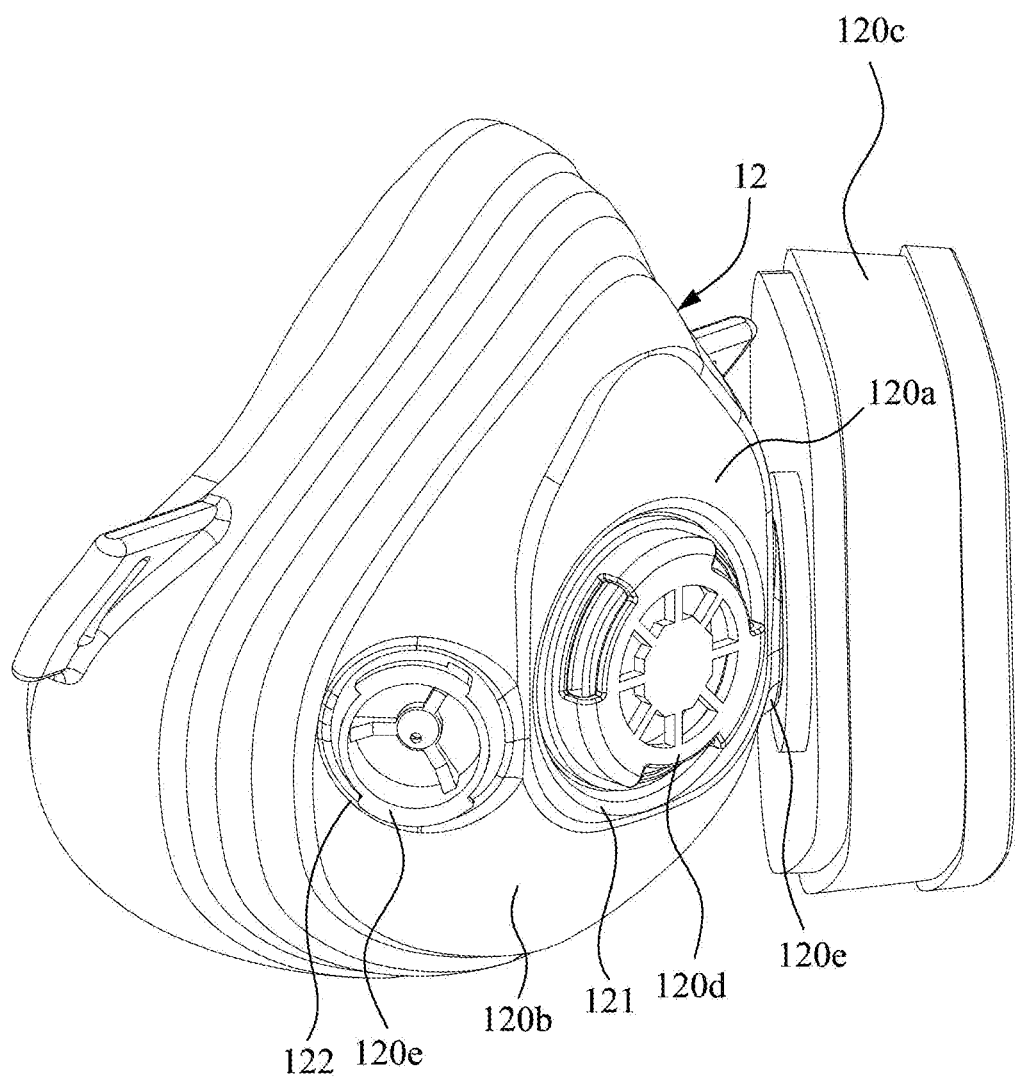
FIG. 6 is a schematic illustrating three dimensional view of the retractable respiratory mask in an extended shape of the present invention according to second embodiment.

As for the way the retractable respiratory mask 10 is folded, referring to FIGS. 3 to 5, the retractable respiratory mask 10 can change the relative position between first bend section 131 and the second bend section 132 by folding over the displacement section 133, such that the filter portion 12 can optionally move away from or close to the worn portion 11, thereby allowing the retractable respiratory mask 10 optionally in deformation between an extended shape 30 and a contracted shape 31.

As shown in FIG. 3, when the first bend section 131 and the second bend section 132 are orderly arranged in the extending direction 20, the displacement section 133 does not enter the accommodation space 112 and making the filter portion 12 away from the worn portion 13 to generate the extended shape 30; since the length of the first bend section 131 (the circumference of the surrounding wall 111) is longer than the length of the second bend section 132 (the circumference of the wall surface of the filter portion 12), the retractable respiratory mask 10 of the extended shape 30 shows a form of being tapered from the worn portion 11 along the extending direction 20; wherein, as for the cross-sectional shape of the retractable respiratory mask 10 of the extended shape 30, please refer to FIG. 4. In the extended shape 30, the arrangement of the cross-sectional shape of the worn portion 11, the filter portion 12, and the retractable portion 13 generally presents as a line 40 that extends along the same direction.

As shown in FIG. 5, when the displacement section 133 is folded over by external force and the displacement section 133 enters the accommodation space 12, the first bend section 131 and the second bend section 132 will be arranged along the direction opposite to the extending direction 20. The filter portion 12 will come close to the worn portion 11 and present the contracted shape 31. Therefore, a corrugation 41 is generated at the cross section of the worn portion 11, the filter portion 12, and the retractable portion 13 (the first bend section 131, the second bend section 132 and the displacement section 133).

Wherein, in order to fold over the displacement section 133 first while encountering external force, as shown in FIGS. 4 and 5, the thickness of the first bend section 131 and the second bend section 132 is smaller than the thickness of the displacement section 133, and the cross-sectional shape of the displacement portion 133 is configured as a central section 133a having a thicker center, and a tapered section 133b having a tapered thickness provided at both ends of the central section 133a; by doing so, when the retractable respiratory mask 10 encounters external force, a stress concentration phenomenon occurs because of the difference in thickness. Thus the first bend section 131 and the second bend section 132 are preferentially bent.

Surely, the present invention does not limit the material design of the retractable portion 13. Therefore, through changing the materials in another embodiment of the present invention, the materials of the first bend section 131 and the second bend section 132 are different from the materials of the displacement section 133. For example, the first bend section 131 and the second bend section 132 are softer than the displacement section 133, such that while encountering external force, the first bend section 131 and the second bend section 132 are easier to be bend and make the displacement section 133 fold over.

Additionally, the deformation of the retractable respiratory mask 10 between the extended shape 30 and the contracted shape 31 requires enough external force to make the displacement section 133 fold over. Therefore, in the present embodiment, the design of the central section 133a of the displacement section 133 with larger thickness makes the retractable respiratory mask 10 to maintain its three-dimensional form/fold-up form while encountering smaller external force that is unable to make the displacement section 133 fold over (for example, the external force is from the weight of the filter member or the weight generated when stacking the respiratory masks). Unlike a conventional mask that is uniform in thickness and can be substantially planar when folded, it does not deform immediately upon encountering external force.

Surely, the present invention also does not limit the number of the displacement section 133 in the retractable portion 13 and bend section used for deforming (the bend section 131 and the bend section 132 in the above-mentioned embodiments). Therefore, in other embodiments, the retractable portion 13 may have a plurality of the displacement sections 133 (e.g., two) as well as a plurality of the bend sections (e.g., three), and the bend sections and the displacement sections 133 are spaced apart from each other.

Finally, regarding the structure of how the retractable respiratory mask 10 is connected to the face of the user, please refer to FIG. 1. In the present embodiment, the retractable respiratory mask 10 further includes an assembly portion 14 that is able to be connected with a strap (not shown). The assembly portion 14 having a pair of extension arms 141, one end of which connects to the wall surfaces of the opposite sides of the worn portion 11, and the other end is used for attaching to the strap, and the extension arm 141 has a distance 12 from the fitting surface 114b.

The present invention does not limit the detailed form and material of the retractable respiratory mask 10, therefore in the embodiments of FIGS. 1 to 5, the retractable respiratory mask 10 is a half mask that does not cover the eyes of the user. In other embodiments, the retractable respiratory mask 10 can be a full face mask that covers the user's eyes (e.g., enlarging the worn portion 111, and providing transparent glasses.); in the embodiment of FIG. 6, the filter portion 12 may be arranged with the two connecting portion 122 and the one connecting portion 121. And in the present embodiment, besides increasing the number, the second connecting portions 122 are separately further provided with a second one-way valve 120e for allowing air to enter the retractable respiratory mask 10 in one single direction (see FIG. 6); yet in order to prevent the interference between the two filter members 120c when the two connecting portions 122 are mounted on the filter members 120c, the two second connecting portions 122 are respectively disposed on opposite sides of the wall surface 120b, while the first connecting portion 121 and the first one-way valve 120d are disposed on the plane 120a.

As can be seen from the above description, through the change in material thickness or in materials, the retractable respiratory mask 10 allow bending happened at the two bend sections (131, 132) first when retractable respiratory mask 10 encounter external force. And the displacement section 133 is folded over into the accommodation space 112 that being surrounded by the worn part 11 to form, and thus the retractable respiratory mask 10 makes a deformation from an extended shape 30 to a contracted shape 31. Therefore, even the retractable respiratory mask 10 requires a certain thickness and a three-dimensional shape to support the weight of the filter having a stronger filtering effect, but the storage height of the retractable respiratory mask 10 also can be reduced by folding up.

What is claimed is:
1. A retractable respiratory mask, comprising:
a worn portion, by a surrounding wall, forming an opening toward an extending direction, and the surrounding wall is arranged with a fitting wall adapted to contact a face of a user;
a filter portion adapted to connect a filter member; and
a retractable portion, being connected between the surrounding wall and the filter portion, composed of a same material as the surrounding wall and the filter portion, able to make a deformation between an extended shape and a contracted shape, such that the filter portion can optionally move away from or close to the worn portion, wherein the retractable portion comprises a first bend section, a second bend section and a displacement section, wherein the first bend section and the second bend section are spaced apart from each other, and the displacement section is connected between the first bend section and the second bend section, and wherein a thickness of the first bend section and a thickness of the second bend section is smaller than a thickness of the displacement section,
wherein the retractable respiratory mask can change a relative position between the first bend section and the second bend section by folding over the displacement section, the extended shape is where the first bend section and the second bend section are orderly arranged in the extending direction, and the contracted shape is presented while the first bend section and the second bend section are arranged along a direction that is opposite to the extending direction.
2. The retractable respiratory mask according to claim 1, wherein a circumference of the first bend section is longer than a circumference of the second bend section, so that the retractable respiratory mask of the extended shape shows a form of being tapered from the worn portion along the extending direction.
3. The retractable respiratory mask according to claim 1, wherein an accommodation space is formed by the surrounding wall of the worn portion, wherein the displacement section of the retractable respiratory mask departs the accommodation space in the extended shape, and the displacement section of the retractable respiratory mask enters the accommodation space in the contracted shape.
4. The retractable respiratory mask according to claim 1, wherein the filter portion has a plane and a wall surface at a periphery of the plane, and wherein the plane is arranged with a first one-way valve for departure of air and a second one-way valve for entry of air.
5. The retractable respiratory mask according to claim 1, wherein the filter portion has a plane and a wall surface at a periphery of the plane, and wherein the plane is arranged with a first one-way valve for departure of air, while the wall surface is arranged with at least one second one-way valve for entry of air.

* * * * *